United States Patent [19]

Mendoza

[11] 4,260,811

[45] Apr. 7, 1981

[54] PROCESS FOR THE REMOVAL OF CYCLIC IMIDIC ESTER IMPURITIES FROM AN ISOCYANATOALKYL ESTER OF AN ORGANIC CARBOXYLIC ACID

[75] Inventor: Abel Mendoza, Midland, Mich.

[73] Assignee: The Dow Chemical Company, Midland, Mich.

[21] Appl. No.: 111,557

[22] Filed: Jan. 14, 1980

[51] Int. Cl.³ .............. C07C 119/042; C07C 119/048
[52] U.S. Cl. .................... 560/218; 260/101; 544/88; 548/239; 560/105; 560/110; 560/248
[58] Field of Search .............. 560/105, 110, 218, 248; 260/453 SP; 548/239

[56] References Cited

U.S. PATENT DOCUMENTS 3,326,929  6/1967  Seeliger .............................. 548/239

FOREIGN PATENT DOCUMENTS 1252099  11/1971  United Kingdom .

OTHER PUBLICATIONS

Nehring et al., Chemical Abstracts, vol. 68: 3922b, (1968).

Primary Examiner—Dolph H. Torrence
Attorney, Agent, or Firm—Michael L. Glenn

[57] ABSTRACT

The level of 2-oxazoline or an oxazine impurity in an isocyanatoalkyl ester of an organic carboxylic acid is reduced by (i) reacting the impurity with an organic acid chloride, a chloroformate, a thiochloroformate, a sulfonyl chloride, phosphoryl chloride, sulfuryl chloride or thionyl chloride and (ii) fractionally distilling the reaction mixture to recover the isocyanatoalkyl ester. As an example, crude 2-isocyanatoethyl methacrylate (IEM) containing 0.19 weight percent 2-isopropenyl-2-oxazoline (IPO) is contacted with terephthaloyl chloride for 0.5 hour at 90° C. The reaction mixture is fractionally distilled to recover 97 weight percent of the IEM containing only 0.02 weight percent IPO.

12 Claims, No Drawings

PROCESS FOR THE REMOVAL OF CYCLIC IMIDIC ESTER IMPURITIES FROM AN ISOCYANATOALKYL ESTER OF AN ORGANIC CARBOXYLIC ACID

BACKGROUND OF THE INVENTION

Field of the Invention

This is a novel process for reducing the cyclic imidic ester content of an isocyanatoalkyl ester of an organic carboxylic acid. In particular, this process relates to the use of an organic acid chloride, chloroformate, thiochloroformate, sulfonyl chloride, phosphoryl chloride or like compound to react preferentially with a cyclic imidic ester at elevated temperatures. The resulting adduct is conveniently removed by distillation.

An isocyanatoalkyl ester can be prepared according to the teachings in British Pat. No. 1,252,099 by reacting a 2-oxazoline or an oxazine in a water-immiscible solvent with phosgene in the presence of an aqueous solution of a hydrogen chloride acceptor. The crude product produced by this method contains small amounts (generally, 0.1–2.0 weight percent) of the 2-oxazoline or the oxazine starting material. The only method employed in the prior art to purify these isocyanatoalkyl esters is fractional distillation, which is effective to remove 2-oxazolines or oxazines, but is not efficient. Frequently, several sequential distillations of the isocyanatoalkyl ester must be employed, to attain product of suitable purity with good recovery. In some utilities, it is critical that the level of cyclic imidic ester impurities is less than that attainable by fractional distillation.

U.S. Pat. No. 3,326,929 teaches that acid chlorides and acid anhydrides can be employed to remove amine and hydroxyl impurities from a 2-oxazoline compound. However, nothing in this reference suggests that these agents can be employed to reduce the 2-oxazoline content of an isocyanatoalkyl ester of a carboxylic acid.

SUMMARY OF THE INVENTION

According to this invention, an isocyanatoalkyl ester of an organic acid containing a cyclic imidic ester impurity is purified in a process comprising:

(a) contacting the cyclic imidic ester-contaminated isocyanatoalkyl ester in the liquid phase with an acid chloride selected from the group consisting of organic acid chlorides, chloroformates, thiochloroformates, sulfonyl chlorides, sulfuryl chlorides, thionyl chloride and phosphoryl chloride, so as to effect substantial reaction of the cyclic imidic ester with the acid chloride; and (b) separating by distillation the isocyanatoalkyl ester from the other components of the reaction mixture produced in step (a).

The term "cyclic" imidic ester" as used herein refers to a 2-oxazoline, a 4H-5,6-dihydro-1,3-oxazine or mixtures thereof. The term "acid chloride" as used herein refers to not only functional derivatives of organic carboxylic acids, but also chloride-containing derivatives of chloroformic acids, thiochloroformic acids, sulfonic acids and like acids, which are included in the aforementioned group of compounds.

DETAILED DESCRIPTION OF THE INVENTION

Isocyanatoalkyl Ester

The isocyanatoalkyl esters of this invention form a known class of compounds having many members, which can be represented by the formula

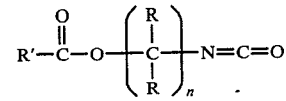

wherein each R is independently hydrogen, alkyl, alkenyl, alkoxy, alkaryl, aralkyl or aryl; n is 2 or 3; and R' is hydrogen, a $C_1$-$C_{17}$ alkyl, a $C_2$-$C_{17}$ alkenyl, a $C_7$-$C_{20}$ aralkyl or a $C_6$-$C_{24}$ aryl. Of course, R in the above formula can represent a wide variety of moieties, such as, methyl, ethyl, cyclohexyl, isopropenyl, vinyl, ethoxy, tolyl, xylyl, phenylethyl or phenyl. Preferably, R at each occurrence is hydrogen. R' also has myriad possible identities, for example, ethyl, methyl, propyl, vinyl, isopropenyl, tolyl or phenyl. Preferably, R' is a $C_1$-$C_4$ alkyl or a $C_2$-$C_4$ alkenyl. More preferably, R' is vinyl or isopropenyl, most preferably isopropenyl. Preferably, n is 2.

The instant process is of course only applicable to isocyanatoalkyl esters containing 2-oxazoline or 4H-5,6-dihydro-1,3-oxazine impurities. This technique is most effective with isocyanatoalkyl esters containing from about 0.05 to about 5.0 weight percent of this cyclic imidic ester impurity. Typically, small amounts of the 2-oxazoline or the starting material will be present in the isocyanatoalkyl ester prepared by the method disclosed n British Pat. No. 1,252,099; the relevant portions of this patent are incorporated herein by reference. In one especially preferred embodiment of this method, a 2-oxazoline in an aqueous solution is added with mixing to a water-immiscible organic solvent containing phosgene to prepare the corresponding isocyanatoalkyl ester. On completion of the phosgenation reaction, the organic phase is conveniently separated, optionally dried with a conventional drying agent, such as $CaCl_2$ or zeolite, and then the acid chloride is introduced to the organic phase in the manner set out hereafter. While the crude isocyanatoalkyl esters prepared in the above-described manner are preferred, the subject process is operable to purify isocyanatoalkyl esters containing cyclic imidic ester impurities prepared by any method.

Cyclic Imidic Ester Impurity

The 2-oxazoline or 4H-5,6-dihydro-1,3-oxazine present in the isocyanatoalkyl ester as an impurity can be represented by the formula

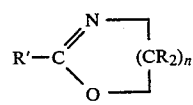

wherein R, n, and R' have the aforementioned possible identities. Generally, R, n, and R' in the formulas for the cyclic imidic ester impurity and the isocyanatoalkyl ester will have the same identities. The amount of 2-oxazoline or oxazine present in the isocyanatoalkyl ester can be readily determined by conventional gas chromatographic analytical techniques employing internal standards.

Acid Chloride Reactants

The acid chloride reactants are generally well-known compounds. Representative reactants include organic acid chlorides of the formula $R_1$-COCl or ClOC-$R_2$-COCl, such as acetyl chloride, propionyl chloride, benzoyl chloride, terephthaloyl chloride and the like; chloroformates of the formula $R_1$OCOCl, such as phenyl chloroformate, ethyl chloroformate, benzyl chloroformate and the like; thiochloroformates of the formula $R_1$SCOCl, such as phenyl thiochloroformate and the like; and sulfonyl chlorides of the formula $R_1SO_2Cl$, such as methanesulfonyl chloride, benzenesulfonyl chloride and the like. In each of the above formulas, $R_1$ is an aliphatic radical having from 1 to about 20 carbon atoms, or an aralkyl, aryl or alkaryl radical having from 6 to about 20 carbon atoms and $R_2$ is a bivalent aliphatic radical having from 1 to about 20 carbon atoms or a bivalent arylene, aralkylene or alkarylene radical having from 6 to about 20 carbon atoms. Generally, it is preferred that the radicals represented by $R_1$ and $R_2$ have at least about 6 carbon atoms, because the adducts of the 2-oxazoline or 2-oxazine and these higher molecular weight acid chlorides are generally more readily separated from the isocyanatoalkyl ester by distillation than are adducts of the lower molecular weight acid chlorides.

Other operable acid chloride compounds include phosphoryl chloride, sulfuryl chloride and thionyl chloride. The preferred acid chloride reactants are terephthaloyl choride, benzoyl chloride, phosphoryl chloride and benzyl chloroformate, with terephthaloyl chloride being most preferred.

Step (a)

The acid chloride reactant and the isocyanatoalkyl ester containing the cyclic imidic ester reactant are brought together with mixing in Step (a), so as to effect intimate contact in a liquid reaction medium. The order of introduction is not critical, but preferably the acid chloride reactant is introduced into the isocyanatoalkyl ester.

The reaction can typically be conducted in the presence or absence of solvents or diluents. In most instances, the isocyanatoalkyl ester will be liquid at the preferred reaction temperatures and the reaction can be readily effected without the addition of solvents or diluents. Examples of such inert diluents (i.e., inert in the instant reaction) include chlorinated alkanes and benzenes, such as methylene chloride, chloroform, ethylene dichloride, chlorobenzene and the like, and inert hydrocarbons, such as benzene, xylene, toluene, cyclohexane and the like. The preferred diluent is methylene chloride. In one preferred embodiment, the isocyanatoalkyl ester is purified in the same organic solvent in which it is prepared.

When the isocyanatoalkyl ester bears a vinyl moiety, it is advantageous to introduce an effective amount of a conventional inhibitor to inhibit vinyl addition polymerization of the isocyanatoalkyl ester. Representative inhibitors include inorganic copper salts (e.g., copper chloride), N-nitrosodiphenylamine, di-beta-naphthol, hydroquinone, p-hydroxydiphenylamine, trinitrotoluene, N,N'-diphenylphenyldiamine, 2,5-di-t-butyl hydroquinone, phenothiazine and monomethyl ether hydroquinone. The amount of inhibitor used can vary, but typically will be from about 0.01 to about 0.2 weight percent based on the weight of the isocyanatoalkyl ester.

The acid chloride compound is advantageously employed in the reaction in an amount from about one-half to about twice the stoichiometric amount. Preferably, from about 90 to about 110 percent of the stoichiometric quantity of the acid chloride is employed. Of course, a much greater excess of the acid chloride reactant can suitably be employed, but is undesirable because it can increase the hydrolyzable chloride content of the purified isocyanatoalkyl ester. The usual stoichiometry of the reaction is that one mole of acid chloride reacts with one mole of the cyclic imidic ester. However, 3 equivalents of the cyclic imidic ester react with each equivalent of phosphoryl chloride and 2 equivalents of the cyclic imidic ester react with each equivalent of terephthaloyl chloride or other diacid chlorides.

The temperature of the liquid reaction medium in Step (a) is desirably in the range from about 25° C. to about 110° C., preferably about 60° C. to about 95° C. The reaction temperature should be maintained in the operable range for a sufficiently long period so as to effect substantial reaction of the cyclic imidic ester with the acid chloride reactant. The term substantial reaction, as used herein, refers to the reaction of at least 25 percent, more preferably at least 50 percent, most preferably at least 90 percent, of the equivalents of the cyclic imidic ester present with the acid chloride. The minimum operable period of contact will vary depending upon the reaction temperature, the identity of the acid chloride, as well as other factors. Typically, a minimum contact period of from about 5 minutes to about 20 minutes is necessary to effect substantial reaction of the cyclic imidic ester with the acid chloride.

The isocyanatoalkyl ester is susceptible to reaction with moisture. For this reason, the reaction mixture is desirably anhydrous. Moreover, the atmosphere above the reaction medium is preferably free from water and is otherwise inert in the reaction. The pressure above the medium is not critical with atmospheric pressure being convenient.

In one preferred embodiment of this invention, immediately following Step (a) of the instant process, the isocyanatoalkyl ester is contacted at from 5° C. to 100° C. with sufficient quantity of a vicinal epoxide compound, such as an epoxy resin or an alkylene oxide, to react with substantially all of the hydrolyzable chloride-containing moieties. The so-called hydrolyzable chlorides are adducts of the isocyanatoalkyl ester and hydrogen chloride, small amounts of which are produced in the preparation of the isocyanatoalkyl ester. These hydrolyzable chloride impurities have an adverse impact on the reaction of the isocyanatoalkyl ester with hydroxyl, mercapto and amino functionalities. The removal of hydrolyzable chlorides in the aforementioned manner is described in my copending application Ser. No. 087,594, filed on Oct. 16, 1979 for "Reduction of Hydrolyzable Impurities in an Isocyanatoalkyl Ester of an Organic Carboxylic Acid", which is incorporated herein by reference. The resulting mixture can then be distilled in the manner described hereafter to recover an isocyanatoalkyl ester containing reduced amounts of both hydrolyzable chloride-containing and cyclic imidic ester impurities.

Step (b)

The isocyanatoalkyl ester can be conveniently recovered from the other components of the reaction mixture resulting from Step (a) by simple distillation of the mixture. Preferably, the distillation of the mixture to recover the isocyanatoalkyl ester occurs contemporaneous with or immediately follows either Step (a) or the optional reaction with the epoxide. Dependent upon the boiling point of the acid chloride and its adduct with the cyclic imidic ester, the acid chloride and its derivative are removed either in a fraction before the isocyanatoalkyl ester or they may be left in the undistilled residue. As mentioned previously, preferably the acid chloride and its adduct are sufficiently high boiling, so that they remain in the undistilled residue. Generally, distillation alone without rectification effects separation of the IEM. The organic diluent, if present, is generally removed in a lower boiling fraction.

The distillation of the isocyanatoalkyl ester is advantageously performed at reduced pressure, preferably less than 10 millimeters of mercury, in order to effect distillation at the lowest temperature possible, thereby minimizing thermal decomposition of the isocyanatoalkyl ester. Generally, temperatures greater than 110° C. should be avoided, if possible. Of course, the distillation of the isocyanatoalkyl ester is advantageously carried out under anhydrous conditions.

EXPERIMENTAL

The following examples will further illustrate the invention. All parts and percentages are by weight unless otherwise specified.

EXAMPLE 1

To a reaction vessel equipped with stirring and temperature indication means were charged 120 grams of 2-isocyanatoethyl methacrylate (IEM), containing 0.19 percent 2-isopropenyl-2-oxazoline (IPO), 100 parts per million (ppm) of monomethyl ether hydroquinone (MEHQ) and 140 ppm hydrolyzable chloride. Terephthaloyl chloride (0.22 gram) was added to the reaction mixture, so as to effect a ratio of 0.5 mole of terephthaloyl chloride for each mole of IPO. The stirred reaction mixture was heated for 30 minutes at 90°-95° C. and then distilled at reduced pressure. The fraction collected at about 60° C. contained 116 grams of IEM having only 0.02 percent IPO and 120 ppm of hydrolyzable chloride.

EXAMPLE 2

In a manner otherwise similar to Example 1, 116 grams of IEM, containing 0.29 percent of IPO, 140 ppm of hydrolyzable chloride and 100 ppm MEHQ, were combined with 0.43 gram of benzoyl chloride and heated at 90°-95° C. for 45 minutes. Thus, this mixture initially contained a 1:1 mole ratio of IPO to benzoyl chloride. Approximately 113 grams of IEM (97 percent recovery) were recovered by distillation at reduced pressure containing 0.03 percent of IPO and 430 ppm of hydrolyzable chloride.

EXAMPLE 3

In a manner otherwise similar to Example 2, 87 grams of IEM, containing the same percentages of IPO, hydrolyzable chloride and MEHQ as in Example 2, were combined with 0.12 gram of phosphoryl chloride (POCl₃) and heated for 45 minutes at 90°-95° C. Thus, this mixture initially contained a 3:1 mole ratio of IPO to POCl₃. About 83 grams of IEM (96 percent recovery), containing 0.03 percent IPO and 340 ppm of hydrolyzable chloride, were recovered by distillation at reduced pressure.

EXAMPLE 4

In a manner similar to Example 1, 968 grams of IEM containing 3.1 percent IPO, 1000 ppm phenothiazine and 100 ppm hydrolyzable chloride were combined with 32.3 grams of ethyl chloroformate and heated for 2 hours at 85° C. The mixture initially contained a 1:1.1 mole ratio of IPO to ethyl chloroformate. The reaction mixture was fractionally distilled through a 10-inch Vigreaux column at reduced pressure. The first 10 grams which distilled were discarded. The next fraction, which weighed 930 grams, was identified as IEM (98 percent recovery) containing 0.04 percent IPO, 570 ppm of hydrolyzable chloride and 0.6 percent of the reaction product of ethylchloroformate and IPO.

Comparative Experiment

In a manner similar to the prior art, 274 grams of IEM containing 1000 ppm MEHQ and 0.02 percent IPO were fractionally distilled at a temperature of 100°–105° C. and a pressure of 2–3 torr through a 10-inch Vigreaux column. The first 66-gram fraction of distillate was determined to contain 0.43 percent of IPO, while the undistilled portion contained 0.04 percent of IPO. The undistilled portion was distilled without further rectification to recovery 204 grams of IEM (74 percent recovery) containing 0.03 percent IPO.

What is claimed is:

1. A process for removing cyclic imidic ester impurities represented by the formula

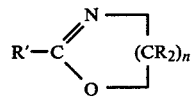

wherein each R is independently hydrogen, alkyl, alkenyl, alkoxy, alkaryl, aralkyl or aryl; n is 2 or 3; and R' is hydrogen, a $C_1$-$C_{17}$ alkyl, a $C_2$-$C_{17}$ alkenyl, a $C_7$-$C_{20}$ aralkyl or a $C_6$-$C_{24}$ aryl, from an isocyanatoalkyl ester of an organic carboxylic acid, said process comprising the steps of:

(a) contacting the cyclic imidic ester-contaminated isocyanatoalkyl ester in a liquid reaction medium with an acid chloride reactant selected from the group consisting of organic acid chlorides, chloroformates, thiochloroformates, sulfonyl chlorides, sulfuryl chloride, thionyl chloride and phosphoryl chloride, so as to effect substantial reaction of the cyclic imidic ester with the acid chloride; and (b) separating by distillation the isocyanatoalkyl ester from the other components of the reaction mixture produced in step (a).

2. The process as described in claim 1 wherein the acid chloride reactant is employed in step (a) in a quantity from about one-half to about twice the stoichiometric amount relative to the cyclic imidic ester.

3. The process as described in claim 1 wherein the acid chloride reactant is employed in step (a) in a quantity from about 90 to about 110 percent of the stoichiometric amount relative to the cyclic imidic ester.

UNITED STATES PATENT AND TRADEMARK OFFICE
CERTIFICATE OF CORRECTION

PATENT NO. : 4,260,811
DATED : April 7, 1981
INVENTOR(S) : Abel Mendoza

It is certified that error appears in the above—identified patent and that said Letters Patent is hereby corrected as shown below:

Column 1, line 61, " "cyclic" imidic ester" " should read -- "cyclic imidic ester" --.

Column 2, line 37, "n" should read --in--.

Column 3, line 33, "choride" should read --chloride--.

Column 4, line 52, after the word "moieties" insert -- present. --.

Column 6, line 24, "0.02" should read --0.20--.

Column 6, line 32, "recovery" should read --recover--.

Signed and Sealed this

Twenty-fifth Day of August 1981

[SEAL]

Attest:

Attesting Officer

GERALD J. MOSSINGHOFF

Commissioner of Patents and Trademarks